(12) United States Patent
Chen et al.

(10) Patent No.: US 9,862,601 B2
(45) Date of Patent: Jan. 9, 2018

(54) PLASMONIC FORCE MANIPULATION IN NANOSTRUCTURES

(75) Inventors: Chang Chen, Leuven (BE); Pol Van Dorpe, Spalbeek (BE); Kai Cheng, Leuven (BE); Tim Stakenborg, Leuven (BE); Liesbet Lagae, Leuven (BE)

(73) Assignees: IMEC, Leuven (BE); Katholieke Universiteit Leuven, KU LEUVEN R&D, Leuven (BE)

(*) Notice: Subject to any disclaimer, the term of this patent is extended or adjusted under 35 U.S.C. 154(b) by 1240 days.

(21) Appl. No.: 13/518,570

(22) PCT Filed: Dec. 24, 2010

(86) PCT No.: PCT/EP2010/070733
§ 371 (c)(1),
(2), (4) Date: Jun. 22, 2012

(87) PCT Pub. No.: WO2011/076951
PCT Pub. Date: Jun. 30, 2011

(65) Prior Publication Data
US 2012/0258544 A1   Oct. 11, 2012

Related U.S. Application Data

(60) Provisional application No. 61/290,046, filed on Dec. 24, 2009.

(30) Foreign Application Priority Data

Dec. 24, 2009 (EP) .................................. 09180753

(51) Int. Cl.
*B82Y 15/00* (2011.01)
*G01N 21/65* (2006.01)
(Continued)

(52) U.S. Cl.
CPC ............ *B82Y 15/00* (2013.01); *C12Q 1/6869* (2013.01); *G01N 33/48721* (2013.01); *G01N 33/538* (2013.01); *Y10T 436/143333* (2015.01)

(58) Field of Classification Search
None
See application file for complete search history.

(56) References Cited

FOREIGN PATENT DOCUMENTS

WO   W02007/041621 A2   4/2007
WO   W02008/021488 A1   2/2008

OTHER PUBLICATIONS

Chen, C. et al. "Focusing Plasmons in Nanoslits for Surface-Enhanced Raman Scattering," Small 2009, 5, No. 24, 2876-2882; Published online: Oct. 8, 2009.*

(Continued)

*Primary Examiner* — Yelena G Gakh
*Assistant Examiner* — Michelle Adams
(74) *Attorney, Agent, or Firm* — McDonnell Boehnen Hulbert & Berghoff LLP (57) ABSTRACT

A system (100) is described for characterizing and/or manipulating molecules. The system may especially be suitable for biological molecules, although the invention is not limited thereto. The system (100) comprises a substrate (110) comprising a nanostructure (120) being suitable for translocation of molecules through the nanostructure (120). It furthermore comprises a means (210) for translocating molecules through the nanostructure (120) and a plasmonic force field generating means (130) adapted for influencing the translocation speed of the particle by applying a plasmonic force field at the nanostructure (120). A corresponding method also is described.

19 Claims, 9 Drawing Sheets

(51) Int. Cl.
  *C12Q 1/68*    (2006.01)
  *G01N 33/487*  (2006.01)
  *G01N 33/538*  (2006.01)

(56) References Cited

OTHER PUBLICATIONS

Fologea, Daniel et al., "Slowing DNA Translocation in a Solid-State Nanopore", Nano Letters, vol. 5, No. 9, 2005, pp. 1734-1737.
Clarke, James et al., "Continuous Base Identification for Single-Molecule Nanopore DNA Sequencing", Nature Nanotechnology, vol. 4, 2009, pp. 265-270.
Choi, Seong S. et al., "Fabrication of a Double Aperture for Near-Field Optical Trapping", Journal of the Korean Physical Society, vol. 45, No. 6, Dec. 2004, pp. 1500-1504.
Dekkar, Cees, "Solid-State Nanopores", Nature Nanotechnology, vol. 2, Apr. 2007, pp. 209-215.
Herrmann, Michael et al., "Near-Field Optical Study of a Protein Transport Kinetics at a Single Nuclear Pore", Nano Letters, vol. 9, No. 9, 2009, pp. 3330-3336.
Trepagnier, Eliane, H. et al., "Controlling DNA Capture and Propagation Through Artificial Nanopores", Nano Letters, vol. 7, No. 9, 2007, pp. 2824-2830.
Sinton, David et al., "Microfluidic and Nanofluidic integration of Plasmonic Substrates for Biosensing", Proc. of SPIE, vol. 7322, 2009, pp. 732206-1 through 732206-13.

\* cited by examiner

PLASMONIC FORCE MANIPULATION IN NANOSTRUCTURES

CROSS-REFERENCE TO RELATED APPLICATIONS

The present application is a 35 U.S.C. 371 National Application of PCT/EP2010/070733 filed Dec. 24, 2010, which claims priority to European Patent Application No. 09180753.7, filed Dec. 24, 2009 and U.S. Provisional Patent Application No. 61/290,046, filed Dec. 24, 2009, the entire contents of which are incorporated entirely herein by reference.

SEQUENCE LISTING STATEMENT

The sequence listing is filed in this application in electronic format only and is incorporated herein by reference in its entirety. The sequence listing text file "09-1295-WO-US_SequenceListing_ST25.txt" was created Jun. 21, 2012, and is 642 bytes in size.

FIELD OF THE INVENTION

The invention relates to the field of analysing and or manipulating molecules such as biological molecules. More particularly, the present invention relates to methods and systems for analysing and/or manipulating molecules using nanostructures.

BACKGROUND OF THE INVENTION

Nanopores can be used for biochemical analysis, mostly structural analysis of linear organic molecules. Whereas originally bio-nanopores were used, these are not stable and typically can only be used once. Consequently, solid-state nanopores which do not suffer from this problem are preferred for nanopore sequencing technology. Solid-state nanopores are holes fabricated artificially in a membrane with diameter in the range (0.1 nm-999 nm). Molecular sequencing in such nanopore relies amongst others on translocation of the target molecule through the nanopore. A particular application of nanopores that is often quoted is DNA sequencing. Transduction and recognition are performed sequentially and in real-time on segments of the molecule. Translocation is achieved passively or (with greater control) actively. Active translocation can be achieved by means of electrophoresis in which a voltage is applied on (two) electrodes placed in fluidic reservoirs separated by the membrane, the resulting electrical field then propels the charged molecule through the pore.

Various electric or electronic interactions can be exploited for sensing in the pore. DNA translocation events are routinely detected by measurement of the ion current through the nanopore. The presence of a DNA molecule in the pore leads to an increase or decrease of the ionic current. More particularly, different base molecules on the DNA strand result in a different blockage effect to the ion flux present at the nanopore. By recording these small changes in impedance, one can get information on the DNA sequence. Provided such measurements can be performed with sufficient sensitivity, information on structural or chemical composition of the molecule could be harvested from ionic current data. In another method, electrodes are mounted in the pore and electronic properties of the molecule are measured there. When a voltage is applied across the electrodes, an electronic current can flow stimulated by quantum mechanical electron tunneling via the electronic states of the molecule. Such mechanism provides chemical specificity. In yet another approach, capacitive modulations are sensed.

One challenge in nanopore sequencing technology is to lower the translocation speed of the DNA strand as the translocation speed currently is so fast that the signals from single base molecules on the DNA strand are not readable. A number of solutions have been provided in the prior art.

In "Slowing DNA translocation in a solid-state nanopore", Fologea describes a technique for reducing the DNA translocation speeds by controlling the environmental conditions, more particularly by controlling the electrolyte temperature, salt concentration, viscosity and the electrical bias voltage across the nanopore. It is shown that adjusting these environmental parameters results in a significant result of the DNA translocation speed.

Another example for decelerating translocation inside a nanopore is chemical functionalisation of the nanopore, as e.g. described by Clake et al. in Nat. Nanotech. 2009 p 265. Chemical interaction between the functionalised nanopore and the DNA to be measured then results in deceleration.

Still another solution for slowing down DNA translocation is the use of an optical tweezer. In this indirect way for controlling DNA translocation, DNA fragments are bound to a bead which can be trapped at or close to the nanopore using the optical tweezer. A disadvantage of such a technique is the requirement for bounding the DNA fragment to the bead, which may influence the DNA, which requires additional equipment and beads, and which requires an additional processing step.

SUMMARY OF THE INVENTION

It is an object of embodiments of the present invention to provide good methods and systems for analysing and/or manipulating molecules using a nanostructure. It is an advantage of embodiments according to the present invention that methods and systems are provide allowing accurate analysis of molecules, e.g. biological molecules. The methods may for example be applicable to nucleic acids or nucleic acid analogs or amino acids.

It is an advantage of embodiments according to the present invention that confinement of the molecules around the nanostructure can be performed with high accuracy.

It is an advantage of embodiments according to the present invention that accurate translocation of molecules can be performed without the need for binding the molecules.

It is an advantage of embodiments according to the present invention that accurate detection of living cells or viruses can be performed. It is an advantage of embodiments according to the present invention that plasmonic force is safe for living cells or viruses, which is often not the case in other techniques used for slowing down translocation speed.

It is an advantage according to embodiments of the present invention that the plasmonic force will drag-molecules towards maximum field-enhanced regions, which is very useful in spectroscopy-based characterization or manipulation methods, such as surface enhanced Raman scattering and surface enhanced Fluorescence. It may advantageously be used in spectroscopy-based DNA sequencing.

It is an advantage of embodiments according to the present invention that plasmonic force can be used in both of ion flux methods and spectroscopy methods, such as for example Raman spectroscopy or fluorescence spectroscopy. This is in contrast to chemical functionalisation for influencing the translocation speed, which is not possible for use in spectroscopy methods. It is an advantage of embodiments according to the present invention that plasmonic force does not have an influence on the ions flux, resulting in the possibility of using measurement of ion flux as an accurate technique for characterizing molecules.

The above objective is accomplished by a method and system according to the present invention.

The present invention relates to a system for characterizing and/or manipulating molecules, the system comprising a substrate comprising a nanostructure being suitable for translocation of molecules through the nanostructure, a means for translocating molecules through the nanostructure, and a plasmonic force field generating means adapted for influencing the translocation speed of the particle by applying a plasmonic force field at the nanostructure. It is an advantage of embodiments according to the present invention that a plasmonic force field can be applied for influencing the translocation speed of molecules, e.g. for reducing the translocation speed of molecules, allowing more accurate measurement of translocation of molecules resulting for example to use the structure for DNA sequencing. It thereby is an advantage that a technique is used that does not substantially affect the molecules to be measured, in contrast to e.g. adjustment of environmental conditions or binding to a bead and trapping.

The plasmonic force field generating means may comprise a metal layer in the substrate for receiving radiation for generating surface plasmons.

The plasmonic force field generating means may comprise a radiation source for generating surface plasmons in the metal layer.

The system may comprise a detection unit for detecting an electric signal indicating a variation in current through the nanostructure, the variation in current being representative of translocation of molecules through the nanostructure.

The means for translocating may comprise an electric field generating means for providing an electrophoresis force on molecules in the system. It is an advantage of embodiments according to the present invention that use can be made of a conventional technique such as electrophoresis for assisting in the translocation of molecules. It furthermore is an advantage of embodiments according to the present invention that the components required for electrophoresis can easily be applied.

The substrate furthermore may comprise at least one of periodic grooves, periodic holes or antenna structures for increasing the plasmonic force field around the nanostructure. It is an advantage of embodiments according to the present invention that additional means, such as for example antennas, can be provided for further enhancing the plasmonic force field in the nanostructure. The plasmonic force field density can be substantially increased in this way.

The nanostructure may be a pore or hole, a slit, a channel or a constriction in a nanochannel. The nanostructure may have a characteristic size smaller than 100 nm, e.g. smaller than 50 nm, e.g. smaller than 10 nm. It is an advantage of embodiments according to the present invention that the small nanostructure allows better spatial confinement.

The substrate may be any of a silicon nanostructure cavity with or without a $SiO_2$ coating, a freestanding membrane with at least one nanostructure or a GaN double-tip structure forming a nanostructure at the tip ends. It is an advantage of embodiments according to the present invention that use can be made of known nanostructure technology for producing the nanostructure according to embodiments of the present invention.

The plasmonic force field generating means may comprise a controller for controlling the plasmonic force field at the nanostructure for operating the nanostructure as switch or valve for the molecules. It is an advantage that switches or valves for molecules can be created based on electrical and/or mechanical forces, e.g. without chemically influencing the molecules to a large extend.

At least a plurality of nanostructures may be present in the substrate and the plasmonic force field generating means may be adapted for providing a different plasmonic force field to some nanostructures. It is an advantage of embodiments of the present invention that a plurality of nanostructures can be provided having different translocation properties, as the latter may be used in separation of molecules having a different length, e.g. making use of their different migration behavior.

The system may comprise a Raman detection system for detecting a Raman signal at the nanostructure. The Raman detection system may be a SERS system.

The system may comprise an analyser for analyzing nucleic acids or its analogs, such as for example RNA, methylated nucleotides or other epigenetic markers. The system may comprise an analyser for analyzing amino acids. Such an analyser may be a processor programmed for detecting or analyzing such molecules.

The present invention furthermore relates to a system for analyzing methylation of nucleic acids or nucleic acid analogs or amino acids, such as for example RNA bases, DNA, methylated nucleotides, epigenetic markers, PNA, LNA, inosine, etc., the system comprising a substrate comprising a nanostructure being suitable for translocation of nucleic acids or nucleic acid analogs or amino acids, through the nanostructure, a means for translocating the molecules through the nanostructure, a plasmonic force field generating means for generating a plasmonic force field at the nanostructure and a surface enhanced Raman spectroscopy detection system for detecting SERS signals. The system furthermore may comprise an analyser, for determining based on the SERS signals a methylation state of the translocated nucleic acids or nucleic acid analogs or amino acids.

The present invention also relates to a method for characterizing and/or manipulating molecules, the method comprising generating a plasmonic force field in a nanostructure by providing radiation to a metal surface of a substrate comprising the nanostructure, the plasmonic force field being for influencing a translocation speed of a particle through the nanostructure, translocating molecules through the nanostructure at a translocation speed influenced by said plasmonic force field, and detecting a signal representative of the translocation of molecules through the nanostructure at a speed influenced by the plasmonic force field.

Detecting may comprise detecting an electric signal representative of a change in current through the nanopore upon translocation of the particle.

Translocating molecules may comprise applying an electrophoresis force to the particle for translocating molecules.

Influencing a translocation speed may comprise reducing the translocation speed of molecules through the nanostructure. It is an advantage of embodiments according to the present invention that due to the reduction of the translocation speed, applications such as DNA sequencing can be performed more accurately.

Influencing of the translocation speed of molecules at the nanostructure may be used for one or more of increasing the trapping chance of molecules at the nanostructure, assembling molecules near the nanostructure or controlling, blocking or providing a passage for molecules through the nanostructure, separating molecules having a different length. It is an advantage of embodiments according to the present invention that due to the influencing of the translocation speed, the trapping chance for trapping the particle may be substantially larger. Similarly, as the translocation speed of molecules can be reduced, assembly of molecules near the nanostructure can more easily be performed. The application of controlling the passage, blocking the passage or providing a passage for molecules through the nanostructure may be applied for controlling the flow of molecules, e.g. in a micro or nano fluidic system. Detecting a signal may comprise detecting a Raman signal representative of the translocation of molecules.

The molecule may be a nucleic acid, nucleic acid analog or amino acid and the method furthermore may comprise analyzing the signal for detecting methylation of the nucleic acid, nucleic acid analog or amino acid.

The present invention furthermore relates to a method for analyzing methylation of nucleic acid, nucleic acid analog or amino acid, the method comprising generating a plasmonic force field in a nanostructure by providing radiation to a metal surface of a substrate comprising the nanostructure, translocating molecules through the nanostructure at a translocation speed influenced by said plasmonic force field, and detecting a signal representative of the translocation of molecules through the nanostructure whereby the detecting is detecting a Raman signal, e.g. a SERS signal. The method also may comprise determining based on the SERS signals a methylation state of the translocated nucleic acid, nucleic acid analog or amino acid.

The present invention also relates to the use of a system as described above for analyzing methylation of nucleic acids or nucleic acid analogs or amino acids. Nucleic acids or nucleic acid analogs may comprise e.g. RNA bases, DNA, methylated nucleotides, epigenetic markers, PNA, LNA or inosine.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF ILLUSTRATIVE EMBODIMENTS

Where in embodiments according to the present invention reference is made to a nanostructure or nanostructures, amongst others nanostructures such as nanostructure gaps are envisaged providing an opening or recess in a substrate or in a channel therein, through which opening or recess at least one nano-dimensioned particle can pass. It may be a nano-scale passageway through which a particle, e.g. molecule, can flow. The nanostructure advantageously may be designed such that the degrees of freedom for the movement of the molecule in the nanostructure is limited to a predefined direction, preferably from one side of the substrate to the other side of the substrate, or in the direction of a nano- or micro-fluidic channel in the substrate. Preferably the movement may be limited to the region through which the particle flows. The nanostructure includes but is not limited to nanopores, nanoslits and nanochannels. It also includes nano-constrictions such as e.g. in a nanofluidics channel, such as for example a passage formed by two nanotips. In embodiments according to the present invention, the terms "nano", "nanosized" or "nanodimension" nanostructures comprise at least one dimension, e.g. a diameter, thickness, width, etc., that has a size smaller than 100 nm, advantageously smaller than 50 nm, such as e.g. smaller than 25 nm or smaller than 10 nm, or smaller than 5 nm.

Where in embodiments according to the present invention reference is made to molecules, reference is made amongst others—the present invention not being limited thereto— nucleic acids, nucleic acid analogs, amino acids, proteins (poly-) and other complex biomolecular entities, polypeptides, peptides, lipids, polysaccharides. Nucleic acids encompass DNA, RNA, single-stranded, double-stranded or triple stranded and any chemical modifications thereof. A nucleic acid may be of almost any length, from a small fragment up to a full length chromosomal DNA molecule.

Where in embodiments according to the present invention reference is made to nucleic acids or nucleic acid analogs, reference may for example be made to RNA bases, DNA, methylated nucleotides, epigenetic markers, PNA, LNA, inosine.

In a first aspect, the present invention relates to a system for characterizing and/or manipulating molecules. The system may be especially suitable for biological molecules, although embodiments of the invention are not limited thereto. The system according to embodiments of the present invention comprises a substrate having at least one nanostructure located in the substrate. The at least one nanostructure thereby is suitable for translocation of the molecules to be characterized or manipulated. The system comprises a means for translocating the molecules through the nanostructure. It is to be noticed that the nanostructures also may include constrictions in lateral nanofluidic channels, so that embodiments of the invention are not limited to flow of molecules through nanostructures through the substrate but also flow of molecules through nanostructures in the substrate. The means for translocation may make use of electrophoresis, although embodiments of the invention are not restricted thereto. For example, also mechanical flow could be considered. According to embodiments of the present invention, the system furthermore comprises a plasmonic force field generating means adapted for influencing, e.g. controlling, the translocation speed by applying a plasmonic force field at the nanostructure.

Figure 1:
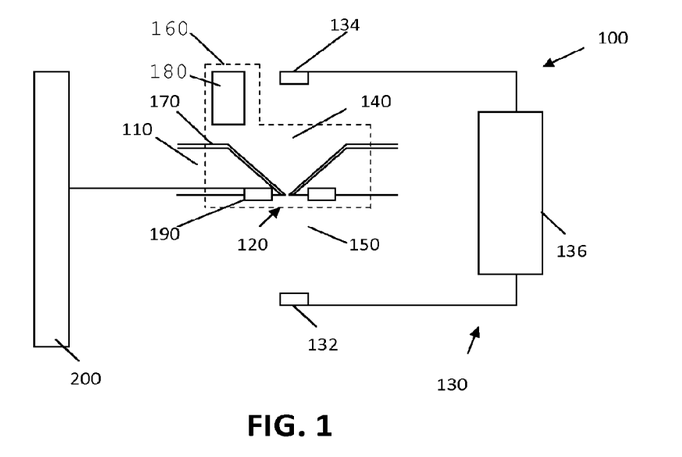
FIG. 1 illustrates a nanostructure system using a plasmonic force field for particle translocation according to an embodiment of the present invention.

By way of illustration, embodiments of the present invention not being limited thereto, a more detailed description of standard and optional features of a system for characterizing or manipulating molecules are given below, with reference to FIG. 1. The system 100 comprises a substrate 110 comprising a nanostructure 120, such as for example a nanopore, a nanoslit, or a nanochannel. In some embodiments, the nanostructure 120 also may be a nanoconstriction in a nanofluidic channel in the substrate. As indicated above, the nanostructure 120 may be a nanoscale passageway through which a molecule can flow. The nanostructure 120 can be round, spherical, rectangular or can have any shape and can have a varying diameter across the thickness of the substrate. In some embodiments, the substrate may be a semiconductor, such as a silicon or germanium, a dielectric substrate such as a quartz substrate, a glass substrate, a polymer substrate, a PMMA substrate, a PDMS substrate, a photoresist layer, etc. The substrate thereby may be provided with an oxide layer, e.g. made by oxidation or deposition, although embodiments are not limited thereto. In some embodiments, the substrate also may be a membrane comprising the nanostructure for particle translocation. The membrane may be a freestanding membrane. Such a membrane could for example be made of a semiconductor material, an insulator, a dielectric material etc. Some particular examples of membranes that could be used are Si, or $SiO_2$, SiN, $Al_2O_3$, GaN, InGaN, AlGaN, GaAs, AlGaAs, PMMA, PDMS etc. In some embodiments, the substrate may consist of a double tip structure which form, for example in a nano-fluidic channel, due to their configuration a nanostructure at the edge of their tips. Such double-tip structure may for example be made from GaN or another semiconductor or dielectric material such as Si, InGaN, AlGaN, AlInGaN, SiO2, SiN, although embodiments of the present invention are not limited thereto.

A number of techniques exist for making nanostructures in a substrate as known by the person skilled in the art.

The system 100 according to embodiments of the present invention furthermore comprises a means 130 for translocating molecules through the nanostructure, also referred to as particle translocator. Translocating may be performed using any suitable driving force. One example thereof is a translocating means 130 based on electrophoresis. The system 100 may for example comprise an electric field generating means for providing an electrophoresis force on molecules in the system. In some embodiments, In some embodiments the system comprises two reservoirs 140, 150, being positioned each at a side of the substrate and being connected via the nanostructure gap. The means for translocating may then be an electric field generating means comprising electrodes 132, 134 in each of the reservoirs 140, 150 over which a voltage is applied. The field generating means may comprise a voltage regulator 136 for controlling the applied voltage. Advantageously, the voltage regulator may be feedback coupled.

The system 100 according to embodiments of the present invention furthermore comprises a plasmonic force field generating means adapted for influencing the translocation speed of the molecules by applying a plasmonic force field at the nanostructure. The plasmonic force field generating means 160 may be adapted for controlling the translocation speed. In one embodiment, the plasmonic force field generating means includes a metal layer 170 in the substrate for generating surface plasmons therein. The substrate may for example have a metal surface or at least partly a metal surface, e.g. by coating with a metal layer. The metal layer may be present at least at the top side or front side of the nanostructure or at both sides. Some examples of metals that could be used are gold, silver, Cu and aluminum. The plasmonic force field generating means 160 may furthermore co-operate with a radiation source or may comprise such a radiation source 180. Examples of radiation sources, which typically may be electromagnetic radiation sources, can be e.g. a light source like a LED, laser, incandescent lamp, etc. In order to optimize generation of surface plasmons and thus the Plasmon force field, the system furthermore may optionally be equipped with a lens system for focusing the radiation on the system, with a coupling system such as for example a grating, etc. According to some embodiments of the present invention, the plasmonic force field generator furthermore may comprise additional field enhancement features at the nanostructure. In one embodiment the enhancement means may be periodic grooves or holes or dimer structures positioned around the nanostructures and acting as antennas so that the field inside the nanostructure is increased. Some examples of dimer structures that may be used are rod dimmers, Bowtie dimmers, etc. Such additional field enhancement features may improve the plasmonic force field. They may create an electromagnetic hotspot, allowing to optimally generate surface plasmons in the nanostructure and thus to optimize the plasmonic force field.

Detection of the particle translocation can be performed in numerous ways. The system 100 may comprise a detector 190 for detecting translocation of molecules. Such a detector may be based on a chemical detection, an electric detection, an optical detection, a spectroscopic detection, etc. In one example, the system is equipped with an electric sensor for sensing ionic current in the nanostructure. As the presence of a particle in the nanostructure leads to an increase or decrease of the ionic current, measurement of the variations in the ionic current provide information regarding particle translocation. Alternatively electronic properties of molecules may be sensed using electrodes provided in the nanostructure. When a voltage is applied across the electrodes, an electronic current can flow stimulated by quantum mechanical electron tunneling via the electronic states of the molecule. Such mechanism provides chemical specificity. In yet another approach, capacitive modulations are sensed. Optical detection is an alternative class of detection mechanisms that could be used. The optical detection may be based for example on surface enhanced Raman scattering (SERS), molecular fluorescence, surface enhanced infrared absorption spectroscopy, etc.

Figure 2:
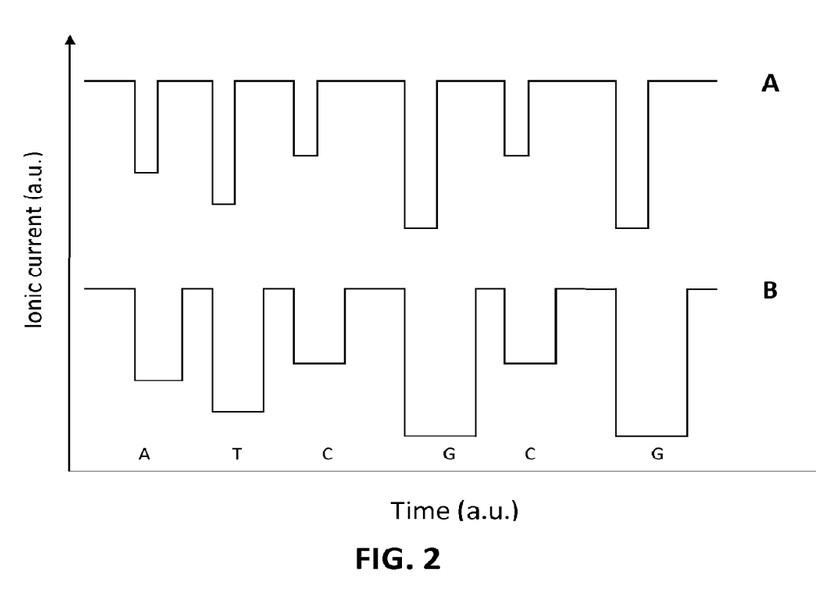
FIG. 2 illustrates an example of sequencing of DNA using a system according to an embodiment of the present invention.

According to some embodiments of the present invention, the system 100 furthermore may comprise a processor 200 for processing the obtained detection results. The processor 200 may for example be adapted for deriving a property of the particle from the detected results. In one example, the processor 200 may be adapted for sequencing a DNA molecule. Some other examples of processing may be deriving a length of a particle, deriving a size of a particle, deriving chemical properties of a particle, deriving a polarity of a particle, deriving a charge of a particle, etc. The processor may operate according to a predetermined algorithm, based on a predetermined rules, using a neural network etc. It may be implemented in hardware as well as in software. By way of illustration, embodiments of the present invention not being limited thereto, an example of sequencing of DNA is shown in FIG. 2. It schematically indicates that passage of DNA molecules through a nanostructure results in a drop of the ionic current, which can be correlated with the passage of a specific nucleotide and that this passage can be significantly slowed down due to the optical forces exerted on the molecule. On top of that, the slowed passage is also beneficial for spectroscopic (optical) techniques. The drawing schematically illustrates the timing for detection of DNA components without (A) and with (B) plasmonic force field slow down of the DNA.

In some embodiments according to the present invention, instead of one nanostructure, a plurality of nanostructures could be provided. The latter may result in making the nanostructures different in behavior such that they can be used as filter.

Figure 3:
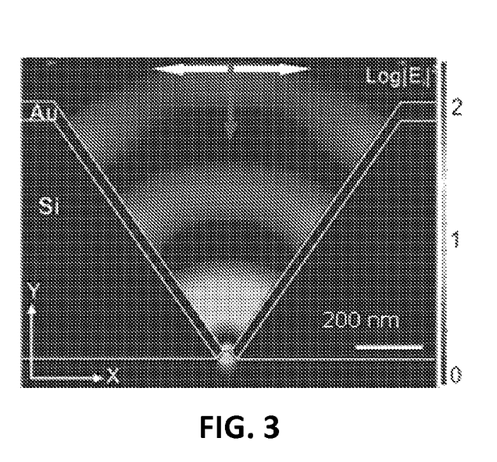
FIG. 3 illustrates a design of part of a system according to an embodiment of the present invention including the logarithm of the electric field intensity present therein.
Figure 4:
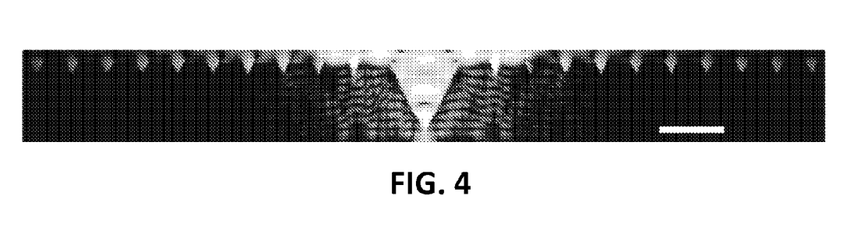
FIG. 4 illustrates an overview of the electric field intensity present in a system according to an embodiment of the present invention.

By way of example, embodiments of the present invention not being limited thereto, an example of a design according to an embodiment of the present invention is shown in FIG. 3, illustrating features and advantages according to embodiments of the present invention. FIG. 3 illustrates a silicon based nanopore cavity, coated with a gold layer. The thickness of the gold layer in the present example is 100 nm. The diameter of the nanopore in the present example is 6 nm. FIG. 3 illustrates the strength of the electric field intensity on a logarithmic scale. A similar illustration is shown in FIG. 4 illustrating the electric field intensity as such for the system shown in FIG. 3. The electric field intensity is high at the nanopore. For these drawings the initial radiation intensity of the radiation used for generating the surface plasmons is normalized to 1 W/µm.

The advantageous effects of the plasmonics force could be explained based on the following concepts, embodiments of the present invention not being restricted thereby. The plasmonic force may create a pull effect. In nanopore DNA translocation, in the presence of the extra electric field (electrophoresis), the electrophoretic force may be estimated at ~0.23 pN/mV. The general voltage used in electrophoresis may typically be ~100 mV, which means the expected force is ~23 pN. Using simulation, of which further results will be provided later, it was established that the plasmonic trapping force at a nanoslit-cavity at 1 W/um excitation power density can reach ~27 pN, opposite to the translocation direction. This means the plasmonic force generated in the nanoslit is somehow comparable with the electrophoretic force and can neutralize its effect, resulting with a slower translocation process. The plasmonic force also may create a push effect from plasmonic force to press the molecules on the edge of the slit to get a friction force. Such friction force also can slow down DNA translocation, as the trap stiffness is ~23 pN/nm.

Figure 5:
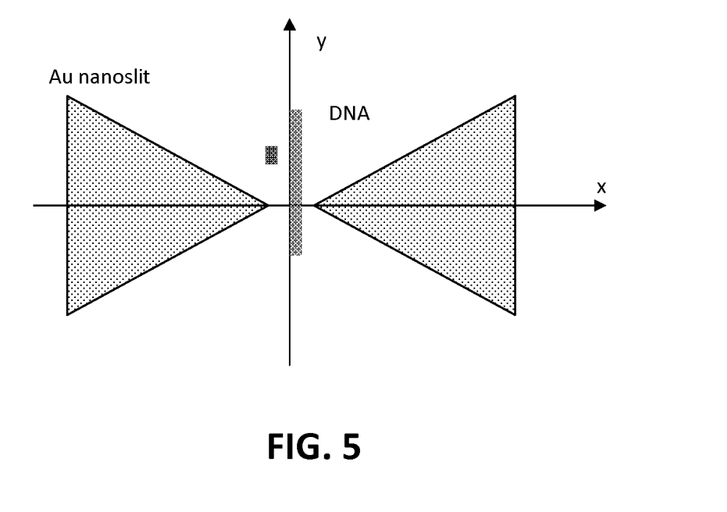
FIG. 5 illustrates a zoom-in schematic diagram of a nanoslit cavity with gold surface as used in simulation experiments for systems and methods according to embodiments of the present invention.

By way of illustration, embodiments of the present invention not being limited thereby, some exemplary simulation results are shown in FIG. 5 to FIG. 9. FIG. 5 illustrates a schematic diagram of the simulation conditions, indicating the 6 nm nanoslit having a Au coated surface. Two DNA fragments are shown used in two simulations, i.e. a 50 nm×2 nm DNA fragment and a 2 nm×2 nm DNA fragment. The DNA fragments are translocated through the nanoslit by electrophoresis. The enhanced optical field inside the nanoslit can generate a strong plasmonic force, which is expected to slow down the translocation speed. The incident light power density is 1 W/m.

Figure 6:
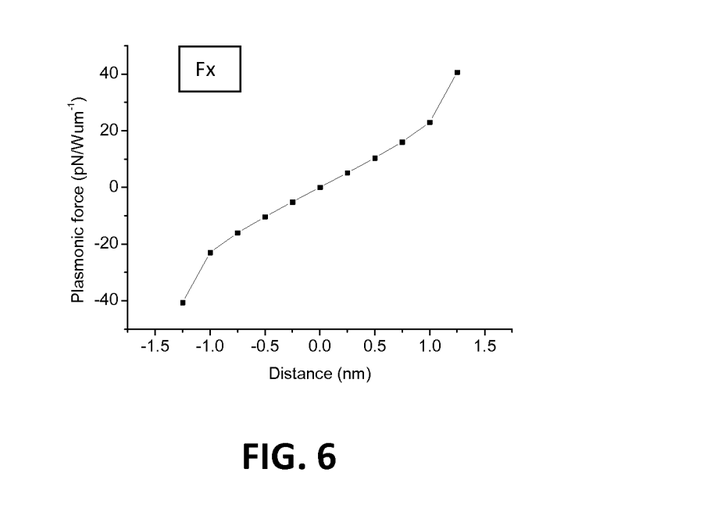
FIG. 6 and FIG. 7 illustrates simulation results for a 50 nm×2 nm DNA fragment indicating the plasmonic force along the x-axis respectively along the y-axis for a nanoslit cavity shown in FIG. 5, illustrating features and advantages according to embodiments of the present invention.
Figure 7:
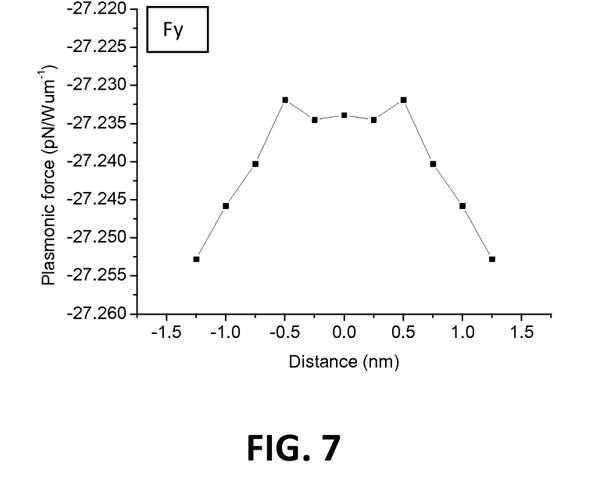

In the first simulation a 50 nm×2 nm DNA fragment is translocated through the nanoslit. FIG. 6 illustrates the plasmonic force $F_x$ on the DNA fragment in the direction along the x axis, while FIG. 7 illustrates the force along the y axis. The plasmonic forces are expressed in $(pN/W\mu m^{-1})$ as function of the distance expressed in nm to the centre of the nanoslit. The DNA position (distance) is changed from left to right. Fx depends on the position of the DNA fragment with respect to the edges of the nanoslit, and it is larger when the DNA fragment is closer to the edge of the nanoslit. Fy is substantially independent on the position, as the length of DNA is much longer than the enhanced field region (~4 nm). Here, the trap stiffness can be obtained from the slope of the force-distance curve (Fx) at ~23 pN/nm at 1 W/um excitation power density, which is about $10^2$~$10^3$ times larger than for known deceleration mechanisms. This can be explained by the much stronger field enhancement inside the nanoslit in the system according to embodiments of the present invention.

Figure 8:
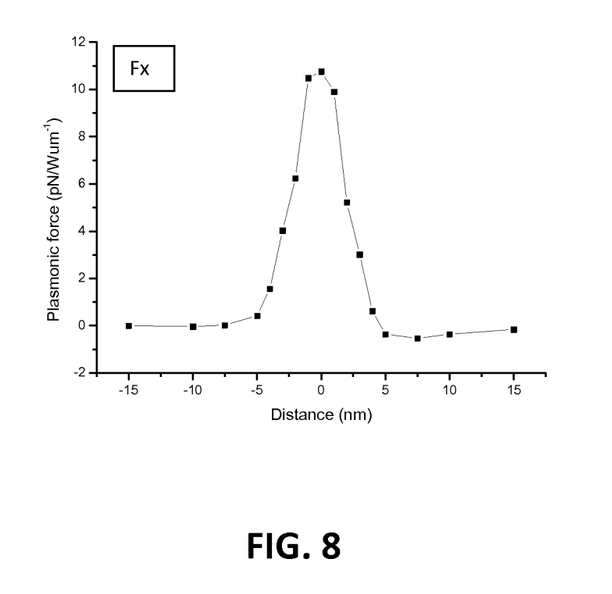
FIG. 8 and FIG. 9 illustrates simulation results for a 2 nm×2 nm DNA fragment indicating the plasmonic force along the x-axis respectively along the y-axis for a nanoslit cavity shown in FIG. 5, illustrating features and advantages according to embodiments of the present invention.
Figure 9:
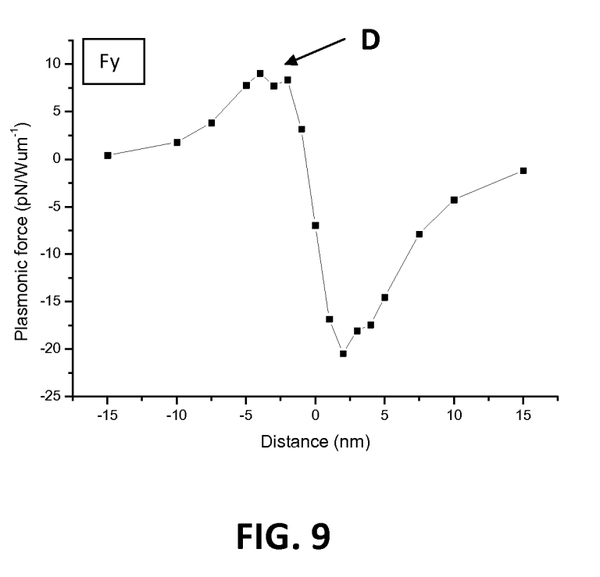

In the second simulation, a 2 nm×2 nm DNA single molecule is translocated through the nanoslit. FIG. 8 illustrates the plasmonic force $F_x$ on the DNA fragment in the direction along the x axis, while FIG. 9 illustrates the force along the y axis. The plasmonic forces are expressed in $(pN/W\mu m^{-1})$ as function of the distance expressed in nm to the centre of the nanoslit. The DNA position (distance) is now changed bottom to top. For small DNA molecules, both of Fx and Fy depend on positions. When the DNA is far away from the enhanced region, there is almost no plasmonic force. However, Fx becomes larger when the DNA is close to the smallest gap, and reaches a maximum value at the smallest gap. Fy behaviors different. From the curves, there are trapping points at ~3 nm away from the smallest gap. This means when a small molecule is around the nanoslit, it will be trapped by the slit and move towards the maximum field-enhanced region (edge of the slit) automatically. The trapping position is indicated by arrow D.

By way of comparison, simulations also were performed without the plasmonic nanoslit-cavity but for DNA molecules close to a metallic surface. The plasmonic force on the 50 nm×2 nm DNA fragment then is more than 100 times weaker, while almost no plasmonic force exists on the 2 nm×2 nm DNA fragment. This illustrates the high spatial resolution that can be obtained using plasmonic force in a nanostructure cavity for small molecules.

The above simulations illustrate for short and longer DNA fragments, features and advantages of embodiments according to the present invention.

By way of further illustration, some exemplary applications are illustrated below, embodiments of the present invention not being limited thereto.

In a first particular example, embodiments according to the present invention are used for decelerating DNA translocation through nanostructures such as nanopores, nanoslits, nanochannels or nanoconstrictions in a nanofluidic channel. Whereas previously high speed of DNA translocation prevented accurate DNA sequencing through solid state nanopores, the latter is overcome by embodiments of the present invention. Using embodiments of the present invention a plasmonic force field can be created for characterizing or manipulating molecules, in one application being deceleration of DNA translocation resulting in the possibility for more accurate DNA sequencing via electrophoresis through a nanostructure. As indicated above, such deceleration could be the effect of both a pulling force counteracting the electrophoresis and a pushing force pressing the molecules against the edges of the nanostructure gaps. From the simulation results indicated above, it can be seen that plasmonic force advantageously allows deceleration which typically is more effective than obtained with prior art techniques.

In a second particular example, embodiments according to the present invention are used for improving trapping chance of molecules at nanostructures. Due to the possibility to slow down the translocation, the chance of trapping can be increased. Trapping, at least temporary, may be performed using the plasmonic force field. Alternatively, other trapping techniques also could be used, assisted by the plasmonic force field generated by antennas around the cavity.

In a third particular example, embodiments according to the present invention are used for separating molecules with a different size. One illustration thereof may be separation of DNA molecules with different lengths. The plasmonic force field used in embodiments according to the present invention results in reduction of the translocation speed allowing accurate measurement of the length of molecules, e.g. DNA molecules, thus providing a manner for separating DNA molecules with different length. In some examples, as the migration speed of molecules and the amount of deceleration that may be obtained typically depends on the size of the molecules, the speed also may be used for separating molecules with a different size. As indicated, separating DNA molecules with different lengths is one illustration. Another illustration is the separation of proteins with different size. For these applications not only the speed of migration is to be taken into account but also polarizability of proteins plays a role. Generally the force exerted scales with the polarizability, which for such molecules, is mainly depending on the size. Nevertheless, the polarizability can be enhanced when the exciting light is resonant with optical molecular transitions. In one embodiment, nanopores that have a different translocation speed behaviour may be used for separating different molecules. In one example molecules can be labeled with metal nanoparticles featuring different resonant wavelengths. When using different nanostructures with different resonant wavelengths, the different particles can be trapped in different nanostructures. In another example, a cascade of different nanostructures, that can "sieve" molecules, as different sizes can be selected. In still another application, the embodiments according to the present invention also may relate to the assembly of molecules near nanostructures. As reducing the translocation speed allows a better manipulation of molecules near the nanostructure, the latter may be used for manipulating the molecules at that position and e.g. assembling molecules at that position.

In still other applications, the embodiments according to the present invention may be used for generating a switch or valve for molecules. By applying a plasmonic force field according to embodiments of the present invention, a nanostructure may prevent the passage of certain molecules, whereas, e.g. in combination with electrophoresis, passage may be free when no plasmonic force field is applied. A variety of applications thus can be provided, whereby manipulation of the molecules is performed to control position and speed of the molecules. The latter may for example be implemented in micro- or nano-fluidics structures, although embodiments of the present invention are not limited thereto.

Figure 11:
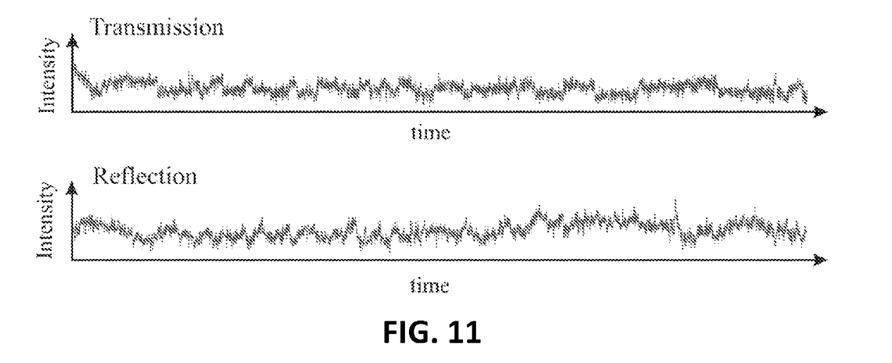
FIG. 11 illustrates transmission and reflection as function of time during a plasmonic force trapping experiment, illustrating features of embodiments of the present invention.
Figure 12:
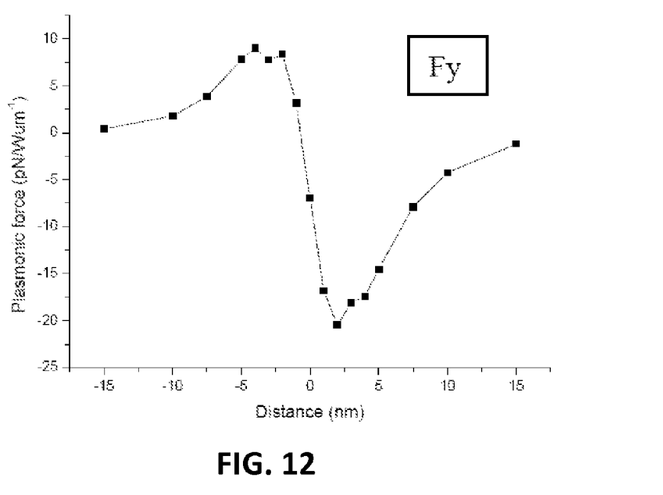
FIG. 12 illustrates a plasmonic force curve with a trapping point, illustrating features of embodiments of the present invention.

By way of example, embodiments of the present invention not being limited thereto, experimental results are shown illustrating features and advantages of the methods and/or systems according to the present invention. Embodiments of the present invention are based on a combination of the realization that particles can be trapped in a nanostructure and the realization that using a plasmonic force the translocation of molecules can be influenced and controlled. The latter allows that molecules e.g. can be analysed. In the first example, an illustration is given from a particle that is trapped in a nanostructure, in the present example being a nanoslit. The nanoslit had a width of 200 nm and a length of 750 nm. It was coated with a 100 nm Au layer. The trapped object were 100 nm polystyrene nanoparticles. The power intensity of the incident laser (wavelength at 1064 nm) was about 2 mW/$\mu m^2$. As shown in FIG. 11, when the PS nanoparticle was trapped by the nanoslit, both the transmission and reflection intensity of the laser irradiating the nanoslit will change. The presence of a dielectric nanoparticle inside the nanoslit will change the surface plasmons inside the gap, resulting in an increased/decreased transmission and a decreased/increased reflection. If the incident light is matched with the transmission resonance of the nanoslit, it enhances the transmission in the presence of a PS bead. On the contrary, when the incident wavelength is not in the resonance, it obtains a weaker transmission. In the present example, the incident wavelength was not matched with the sample nanoslit and when it trapped a PS bead, the transmission intensity was be reduced. From the time curves in the figure, the trapping events were be demonstrated by the oppositely changes of the transmission and reflection intensities. When there is an intensity dip in the transmission and an intensity jump in the reflection, it is a trapping event. FIG. 12 illustrates the trapping point in a plasmonic force versus distance curve. The trapping point is at the cross of the dash line (plasmonic force equals zero) and the force curve.

In another aspects, embodiments of the present invention relate to a method and system for analyzing methylation of nucleic acids or nucleic acid analogs or amino acids. Methylation may for example provide important information regarding epigenetics, such as for example provide information regarding aging, presence of cancer or providing protection against invading molecules like DNA, etc. For example, tumor cells are typically characterized by hypermethylation of CpG islands. Surface enhanced Raman spectroscopy (SERS) using a plasmonic nanostructure can according to embodiments of the present invention be used for detecting or analyzing methylation. According to embodiments of the present invention, a system is disclosed for analyzing methylation of molecules, the system comprising a substrate comprising a nanostructure being suitable for translocation of molecules through the nanostructure, a means for translocating the particles through the nanostructure, a plasmonic force field generating means for generating a plasmonic force field at the nanostructure and a surface enhanced Raman spectroscopy detection system for detecting SERS signals. The system furthermore may comprise an analyser for determining based on the SERS signals a methylation state of the translocated molecules, e.g. nucleic acids or nucleic acid analogs or amino acids. Determining a methylation state may comprise for example determining whether methylation is present or not, determining a proportion of the methylated bases, determining the presence of dangerous genomes, determining the type of methylation, etc. Furthermore, similar determination can be obtained for protein (histone) methylation. Using a plasmonic nanostructure chip as SERS substrate thus allows obtaining single molecule level sensitivity in the nanostructure and this principle can be used for analyzing molecules, in one example for analyzing methylation of molecules. Such an analyser may for example be a processor in which analysis is based on comparison of detection results with previously calibrated data based on previously performed experiments, based on a neural network, using a predetermined algorithm or using a look up table. The processor may be software or hardware based and evaluation may be performed automated or automatically using a computer. The processor may thus comprise computing power. In one exemplary embodiment, the nanostructure chip is positioned in between two reservoirs such that the only channel for mass transport is the nanostructure. In one example clinical DNA samples are dissolved in one of the reservoirs and using an electrophoresis method, the fluid is driven through the nanostructure, with migration of the clinical DNA towards the anode. Characteristic SERS signals can be recorded at the SERS detection region in the nanostructure, the SERS detection signals being highly concentrated. Based on the SERS spectra from the clinical DNA samples, a difference can be made between methylated DNA samples and non-methylated DNA samples. Single DNA strand translocating through the nanopore thereby are detected, due to the confinement of the DNA translocation due to the physically small size of the nanopore. Such single DNA strand translocation can thus provide clinical diagnosis results. It is an advantage of embodiments of the present invention that different DNA samples can be detected, without the need for perfect purification. It is an advantage of embodiments according to the present invention that they methods and systems are provided for direct detection of DNA methylation. Direct detection of DNA methylation has the advantage of requiring less complex steps compared to e.g. Bisulphite sequencing, often used at present for detecting DNA methylation. As indicated above, embodiments of the present invention also relate to a method for analyzing methylation of molecules, such as nucleic acids or nucleic acid analogs or amino acids, the method comprising generating a plasmonic force field in a nanostructure by providing radiation to a metal surface of a substrate comprising the nanostructure, translocating molecules through the nanostructure at a translocation speed influenced by said plasmonic force field, and detecting a signal representative of the translocation of molecules through the nanostructure whereby the detecting is detecting a Raman signal, e.g. a SERS signal. The method also may comprise determining based on the SERS signals a methylation state of the translocated DNA molecules. It is to be noticed that features and advantages of embodiments according to the present aspect may be completed or altered with feature of embodiments described elsewhere in the present invention. For example—embodiments of the present invention not being limited thereto—the plasmonic force may be used for influencing and/or controlling the translocation speed of the molecules.

Figure 13:
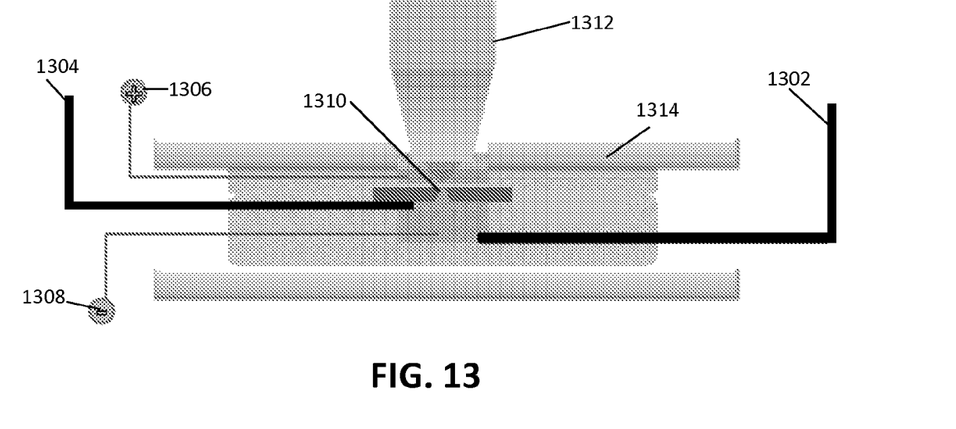
FIG. 13 shows a schematic representation of a methylation detection system, according to an embodiment of the present invention.

By way of illustration, embodiments of the present invention not being limited thereto, some experimental results indicating features and advantages of methods and/or systems for analyzing methylation are discussed below. In FIG. 13, an exemplary system for performing methylation detection is shown. The system illustrates a feed-in channel 1302 and a waste channel 1304 and an electrode system 1306, 1308 between the top and back reservoirs for providing electrophoresis guide molecular translocation through the nanostructure 1310. The SERS detection system according to the present example comprises a laser (not shown) focused at the nanostructure 1310 using an objective lens 1312 which in the present example is a water immersing objective lens. In the present example, the SERS signal is collected using the same objective lens 1312. The device, which may be a microfluidic structure made in PDMS, further may comprise a sealing component 1314. In the present example, the Raman setup used is LabRAM HR from Horiba Scientific, Ltd. Analytes were only added into the backside reservoir. According to the high spatial resolution of the SERS inside the nanoslit (a few nanometers in the vertical direction), the Raman signal of molecules can only be recorded when the molecules are translocating through the nanoslit.

Figure 14:
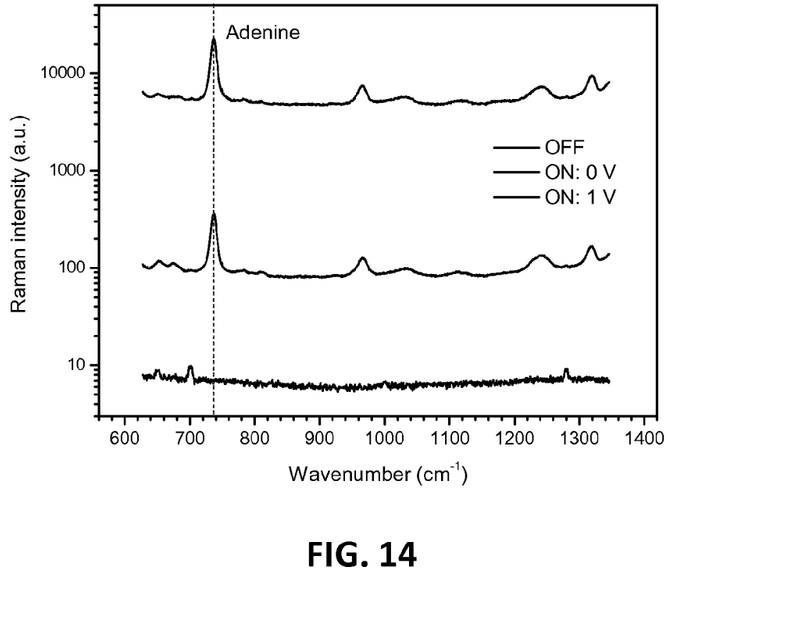
FIG. 14 shows the detection of Adenine translocation as can be obtained using a method according to an embodiment of the present invention.

In a further particular example, the detection of translocation of adenine is illustrated. Adenine is a kind of base molecule of DNA. Without electrophoresis, no SERS signal can be seen. When the voltage is added for 5 minutes at a voltage of 1V, the signal can be recorded even after switch off of the voltage (i.e. at 0V). When the voltage is maintained the detected SERS signal intensity is the highest (i.e. at 1V). The latter illustrates that adenine is indeed translocated through the nanostructure. The flux of adenine also influences the Raman intensity. A larger flux results in a more intense signal. In the experiment the concentration of adenine is $10^{-3}$M, the laser intensity is 7 mW/$\mu$m$^2$ and the wavelength used is 785 nm. The integration time is 60 s. The small DNA base molecules (adenine) translocation thus was detected inside the nanoslit by SERS. The experimental results before application of the voltage (OFF), during application of the voltage (ON: 1V) and after the application of the voltage (ON: 0V) is shown in FIG. 14.

Figure 15:
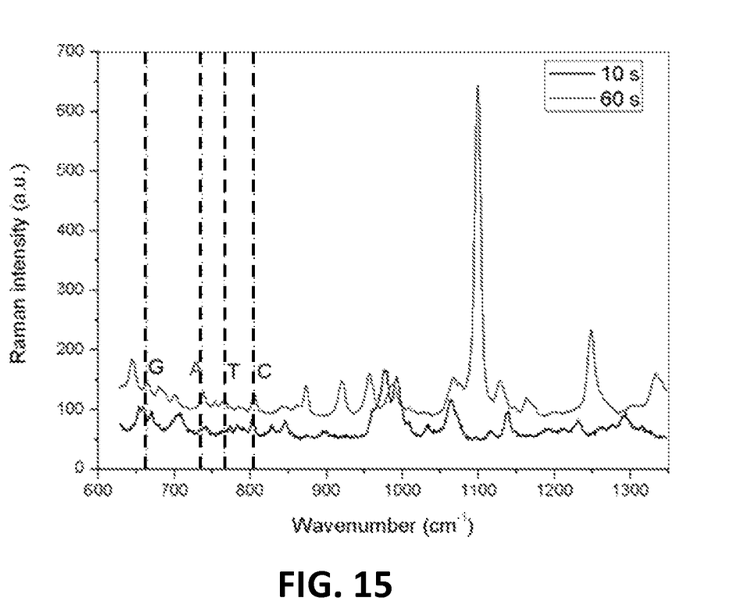
FIG. 15 shows the detection of DNA oligo translocation as can be obtained using a method according to an embodiment of the present invention.

In another example, detection of DNA oligos is illustrated. The sequence of DNA oligos TTCACAGGTACTG-GATTTGATTGTGACAGTCATTCCTGTCAACTGAG-CAC also referred to as 5onct is used. The concentration used is $10^{-8}$ M and the laser power used is 7 mW/$\mu$m$^2$ at a wavelength of 785 nm. The results are shown in FIG. 15 for integration times of 10 s and 60 s. The Raman spectrum of the DNA molecule are shown. Considering the integration time is much longer than the DNA oligo translocation speed which is milliseconds level, the resultant SERS spectrum is a summation of all translocation events during the integration time. All Raman bands of these four DNA oligo molecules can be detected.

Figure 16:
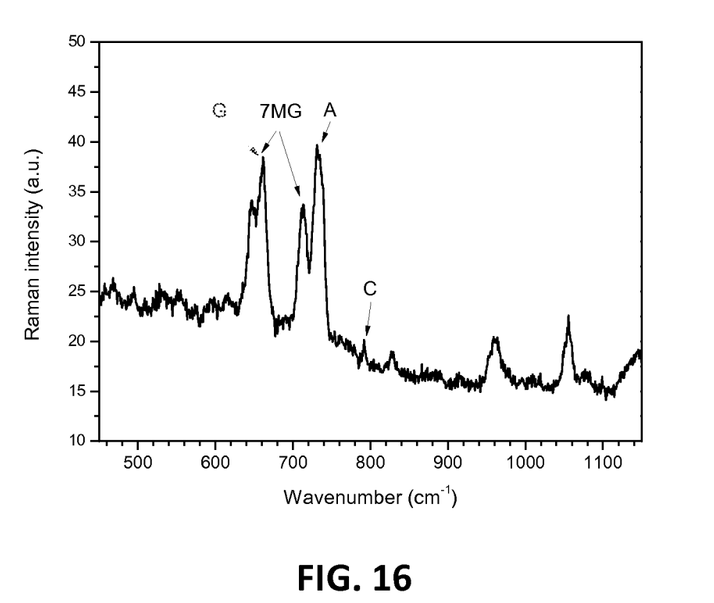
FIG. 16 shows the detection of methylated base molecules, illustrating features of embodiments according to the present invention.

In still another example, a mixture of methylated guanine, adenine and cytosine is added into the back reservoir. A Raman spectrum of this mixture is shown in FIG. 16. Due to the different wavenumber of these Raman bands, the methylated guanine can be recognized easily from adenine and cytosine. Compared with the non-methylated guanine, the methylated guanine has a secondary Raman band at about 710 cm$^{-1}$. The concentration of adenine used was $10^{-4}$M, with a laser power of 7 mW/$\mu$m$^2$ and at a wavelength of 785 nm. The integration time used was 10 s. In conclusion it can be seen that methylated DNA bases can be recognized from a mixture of several kinds of DNA bases, such as 7MG, A or C. In one aspect, the present invention also relates to the use of a system as described in one or more embodiments of the first aspect for one or more applications as described by way of example above. More generally, the present invention also relates to the use of a system as described in one or more embodiments of the first aspect for characterizing and/or manipulating molecules using a plasmonic force field for controlling translocation of the molecules through a nanostructure gap.

Figure 10:
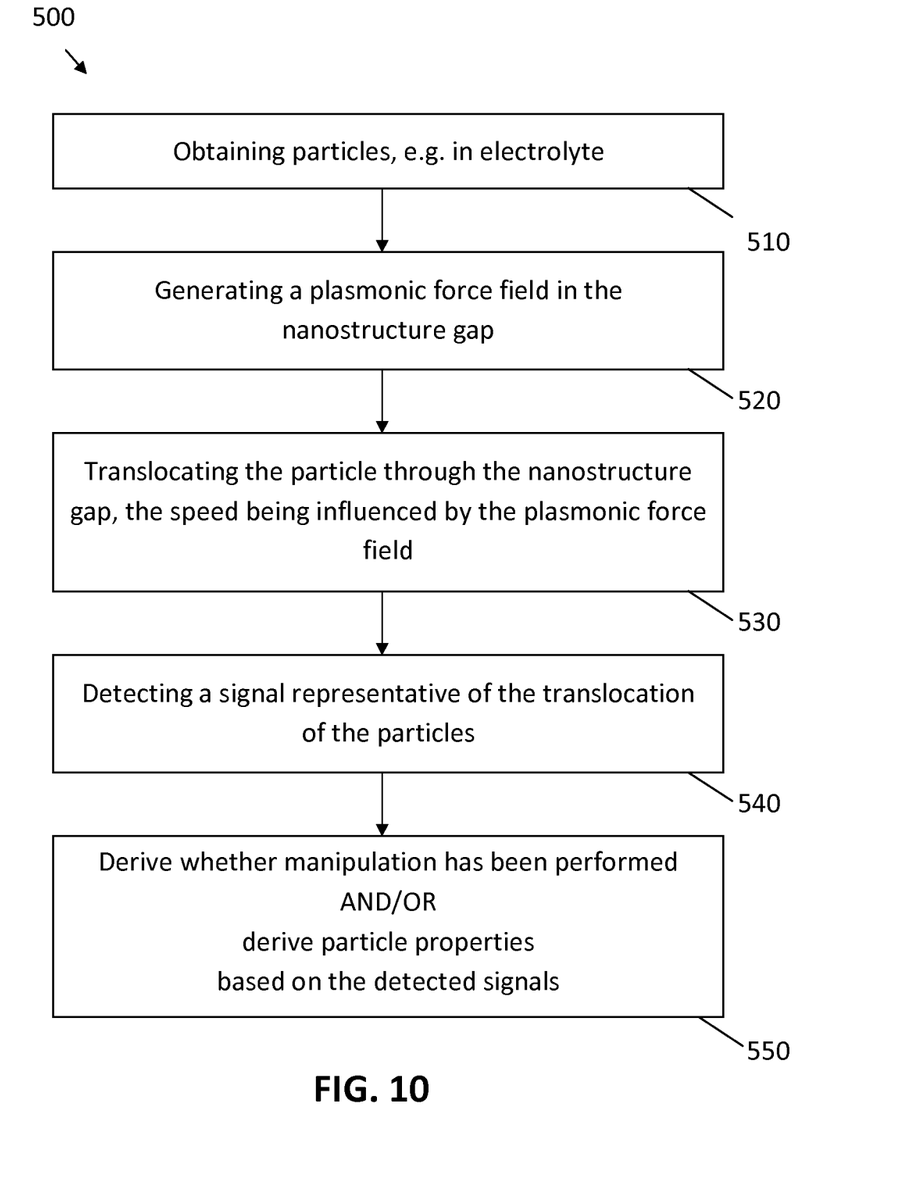
FIG. 10 illustrates a flow chart indicating standard and optional steps of a method for characterizing and/or manipulating molecules according to an embodiment of the present invention.

In one aspect, the present invention also relates to a method for characterizing and/or manipulating molecules. The method may be especially suitable for characterizing and/or manipulating biological molecules, including for example characterizing living cells or sequencing DNA, although embodiments are not limited thereto. By way of illustration, embodiments of the present invention not being limited thereto, a flow-chart illustrating standard and optional steps of a method according to an embodiment of the present invention is shown in FIG. 10. The method 500 may be initiated by obtaining 510 one or more molecules in an electrolyte. The molecules may be biological molecules or other molecules, as described above. In a following step, the method may comprise generating 520 a plasmonic force field in a nanostructure gap by providing radiation to a metal surface of a substrate comprising the nanostructure gap, the plasmonic force field being for influencing a translocation speed of a particle through the nanostructure gap. In some embodiments, the translocation speed also may be controlled by the plasmonic force. Typically, the plasmonic force field may be applied for slowing down the particle in counteracting a translocation force applied to the particle. The method also comprises translocating 530 molecules through the nanostructure at a translocation speed influenced by the plasmonic force field. Translocating thereby may be performed using electrophoresis, i.e. by applying an electrophoresis force to the particle to be translocated. The method further comprises detecting 540 a signal representative of the translocation of molecules through the nanostructure at a speed influenced by the plasmonic force field. Detecting may be detecting an electric signal representative of a change in current through the nanopore upon translocation of the particle. Detecting may be performed to derive whether the particle manipulation has been performed or to derive, from these measurements, characteristics of the particle translocated. This is indicated in step 550. Detection may for example comprise detecting a Raman signal, e.g. by collecting SERS signals. Detecting Raman signals, e.g. SERS signals, may be for example performed using a system as described above, although embodiments of the present invention are not limited thereto. Some applications that may be performed using the method can be increasing the trapping chance of molecules at the nanostructure gap, assembling molecules near the nanostructure gap or controlling, blocking or providing a passage for molecules through the nanostructure gap, separating molecules having a different length, etc.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated. For example, whereas often reference is made to DNA, examples and embodiments also more generally relate to nucleic acid or nucleic acid analogs or amino acids.

The invention claimed is:

1. A system for characterizing and/or manipulating particles, the system comprising:
a substrate comprising a nanostructure being suitable for translocation of particles through the nanostructure;
a means for translocating particles through the nanostructure via a translocation force; and
a plasmonic force field generating means adapted for influencing the translocation speed of a particle by applying a plasmonic force field at the nanostructure, wherein the plasmonic force field generating means comprises a metal layer on the substrate and a radiation source for generating surface plasmons in the metal layer so as to adjust the translocation force, and further comprises a controller comprising a processor and instructions stored in memory that when executed by the processor cause the plasmonic force field generating means to carry out functions including control of the plasmonic force field at the nanostructure such that the nanostructure operates as a switch or valve for the particles.

2. The system according to claim 1, the system comprising a detection unit for detecting an electric signal indicating a variation in current through the nanostructure, the variation in current being representative of translocation of particles through the nanostructure.

3. The system according to claim 1, wherein the substrate furthermore comprises at least one of periodic grooves, periodic holes or antenna structures for increasing the plasmonic force field around the nanostructure.

4. The system according to claim 1, wherein the nanostructure is a pore or hole, a slit, a channel, or a constriction in a nanochannel.

5. The system according to claim 1, wherein the substrate comprises any of a silicon nanostructure cavity, a freestanding membrane with at least one nanostructure, or a GaN double-tip structure forming a nanostructure at the tip ends.

6. The system according to claim 1, wherein a plurality of nanostructures are present in the substrate, wherein the plasmonic force field generating means is adapted for providing a different plasmonic force field to at least some of the nanostructures.

7. The system according to claim 1, the system comprising a Raman detection system for detecting a Raman signal at the nanostructure, wherein the Raman detection system is a SERS system.

8. The system according to claim 1, the system furthermore comprising an analyser configured to analyse nucleic acids or nucleic acid analogs.

9. The system according to claim 8, wherein the nucleic acids or nucleic acid analogs comprise any of RNA, methylated nucleotides, or other epigenetic markers.

10. The system according to claim 1, the system furthermore comprising an analyser for analyzing amino acids.

11. The system according to claim 1, wherein the radiation source comprises at least one of a light-emitting diode (LED), a laser, or an incandescent lamp, wherein the radiation source is configured to emit light, and wherein at least a portion of the emitted light is incident upon the nanostructure.

12. The system according to claim 1, further comprising a lens system configured to focus radiation emitted by the radiation source onto the metal layer of the substrate.

13. A method for characterizing and/or manipulating particles, the method comprising:
generating a plasmonic force field in a nanostructure of a substrate by providing radiation to a metal surface on the substrate, the plasmonic force field acting to adjust a translocation speed of a particle through the nanostructure;
translocating particles through the nanostructure at a translocation speed influenced by the plasmonic force field;
controlling the plasmonic force field at the nanostructure such that the nanostructure operates as a switch or valve for the particles; and
detecting a signal representative of the translocation of particles through the nanostructure at a speed influenced by the plasmonic force field.

14. The method according to claim 13, wherein the detecting comprises detecting an electric signal representative of a change in current through a nanopore upon translocation of the particles.

15. The method according to claim 13, wherein translocating particles comprises applying an electrophoresis force to the particles.

16. The method according to claim 13, wherein acting to adjust the translocation speed comprises reducing the translocation speed of particles through the nanostructure.

17. The method according to claim 13, wherein acting to adjust the translocation speed of the particle is used for one or more of increasing a trapping chance of particles at the nanostructure, assembling particles near the nanostructure, separating particles having a different length, or controlling, blocking or providing a passage for particles through the nanostructure.

18. The method according to claim 13, wherein detecting a signal comprises detecting a Raman signal representative of the translocation of particles.

19. The method according to claim 13, wherein the particle comprises a nucleic acid, nucleic acid analog, or amino acid, and wherein the method furthermore comprises analyzing the signal for detecting methylation of the nucleic acid, nucleic acid analog, or amino acid.

* * * * *

SEQUENCE LISTING

<160> NUMBER OF SEQ ID NOS: 1

<210> SEQ ID NO 1
<211> LENGTH: 50
<212> TYPE: DNA
<213> ORGANISM: Artificial sequence
<220> FEATURE:
<223> OTHER INFORMATION: Oligos

<400> SEQUENCE: 1
ttcacaggta ctggatttga ttgtgacagt cattcctgtc aactgagcac                50